United States Patent [19]
Müller et al.

[11] Patent Number: 5,977,378
[45] Date of Patent: Nov. 2, 1999

[54] PROCESS FOR THE PREPARATION OF 1-ALKYL-PYRAZOLE-5-CARBOXYLIC ACID ESTERS

[75] Inventors: Nikolaus Müller, Monheim; Lutz Heuer; Johannes Kanellakopoulos, both of Dormagen; Andreas Sattler, Düsseldorf; Klaus-Peter Heise, Odenthal, all of Germany

[73] Assignee: Bayer Aktiengesellschaft, Leverkusen, Germany

[21] Appl. No.: 09/004,247

[22] Filed: Jan. 8, 1998

[30] Foreign Application Priority Data

Jan. 16, 1997 [DE] Germany ............... 197 01 277

[51] Int. Cl.$^6$ ................................ C07D 231/14
[52] U.S. Cl. ...................................... 548/374.1
[58] Field of Search ............................ 548/374.1

[56] References Cited

U.S. PATENT DOCUMENTS 5,462,960  10/1995  Barth et al. ............... 514/406

FOREIGN PATENT DOCUMENTS

| 0 029 363 A1 | 5/1981 | European Pat. Off. . |
| 0 029 364 A1 | 5/1981 | European Pat. Off. . |
| 0 463 756 A1 | 1/1992 | European Pat. Off. . |
| 0 526 004 A1 | 2/1993 | European Pat. Off. . |
| 0 854 142 | 1/1998 | European Pat. Off. . |
| 1 927 429 | 5/1968 | Germany . |
| 264 210 A5 | 1/1989 | Germany . |
| 184940 | 11/1984 | Hungary . |

OTHER PUBLICATIONS

Patent Abstracts of Japan (JP 61 040266 A) vol. 10, No. 199 (C–359) [2255], Jul. 11, 1986.
Patent Abstracts of Japan (JP 59 196868 A) vol. 9, No. 59 (C–270) [1782], Mar. 15, 1985.
Patent Abstracts of Japan (JP 07 118238 A) vol. 0 95, No. 008, Sep. 29, 1995.
W. Theilheimer "Synthetic Methods of Organic Chemistry" 1962, S. Karger XP002058626, vol. 16, 428; p. 204.
W. Theilheimer "Synthetic Methods of Organic Chemistry" 1984, S. Karger XP002058627, vol. 38, 412; p. 166.
W. Theilheimer "Synthetic Methods of Organic Chemistry" 1975, S. Karger XP002058628, vol. 2, 368; p. 128.
W. Theilheimer "Synthetic Methods of Organic Chemistry" 1952, S. Karger XP002058629, vol. 6, 403; p. 148.
A.R. Katritsky et al.: "Comprehensive Heterocyclic Chemistry", 1984, Pergamon Press XP002058630, vol. 5, pp. 277–282.
Chem. Ber. 59, (1926), p. 1282.
Chem. Ber. 59, (1996), p. 603.
J. Prakt. Chem. 26, (1930), p. 198.
Austr. J. Chem. 36, (1983), pp. 135–147.
Seki et al., Chem. Pharm. Bull., 32(4), pp. 1568–1577, 1984.

*Primary Examiner*—Laura L. Stockton
*Attorney, Agent, or Firm*—Joseph C. Gil; Carol Marmo; Thomas W. Roy

[57] ABSTRACT

1-alkyl-pyrazole-5-carboxylic acid esters are prepared by reacting the enolate of a 2,4-diketocarboxylic acid ester with an N-alkylhydrazinium salt in the presence of a solvent. This process allows a particularly economic preparation of 1-alkyl-pyrazole-5-carboxylic acid esters in a simple manner and with only little formation of undesirable isomers.

14 Claims, No Drawings

PROCESS FOR THE PREPARATION OF 1-ALKYL-PYRAZOLE-5-CARBOXYLIC ACID ESTERS

The present invention relates to a process for the preparation of 1-alkyl- and, in particular, also 1,3-dialkyl-pyrazole-5-carboxylic acid esters from the enolate of 2,4-dicarboxylic acid esters and N-alkylhydrazinium salts.

It is already known to prepare 1-alkyl-pyrazole-5-carboxylic acid esters by alkylation of pyrazole-3-carboxylic acid esters with alkylating agents (for example alkyl halides, dialkyl sulfates or alkyl tosylates).

EP-OS (European published specification) 463 756 and EP-OS (European published specification) 526 004 thus describes the preparation of ethyl 1-methyl-3-n-propyl-pyrazole-5-carboxylate by reaction of ethyl 3-n-propylpyrazole-5-carboxylate with dimethyl sulfate. A mixture of the two isomeric N-methyl-pyrazoles, which must be separated by means of chromatographic methods with great expenditure, is evidently formed here.

DE-OS (German published specification) 19 27 429 describes the preparation of ethyl 1-methyl- and 1-ethyl-3-propyl-pyrazole-5-carboxylate from ethyl 3-propyl-pyrazole-5-carboxylate by alkylation with dimethyl sulfate or triethyloxonium tetrafluoroborate. There is no information on possible occurrence of isomers, their separation or the total yield of the desired product, although on the basis of the literature known up until that time, the formation of isomer mixtures must always be expected. Methylation of methyl 3,4-dimethyl-pyrazole-5-carboxylate with methyl iodide and sodium methylate, as an auxiliary base, thus leads to a mixture of the isomeric trimethylpyrazolecarboxylic acid esters, which it was possible to separate into the isomers only after "rectification several times" (J. Prakt. Chem. 126, 198 (1930)). Ethylation of ethyl 3-methylpyrazole-5-carboxylate with ethyl bromide/sodium in absolute alcohol gives a mixture of ethyl 1-ethyl-3-methyl-pyrazole-5-carboxylate and ethyl 1-ethyl-5-methyl-pyrazole-3-carboxylate in a ratio of about 1:3. That is to say, the 1,3-dialkylisomer, which is often desired, is formed in a significant deficit and is obtained in the pure form only after distillation three times (Chem. Ber. 59, 603 (1996)).

The other method which is to a large extent widespread for the preparation of 1-alkyl-pyrazole-5-carboxylic acid esters is reaction of 2,4-diketocarboxylic acid esters with N-alkyl-hydrazines. Here also, isomer mixtures are obtained which as a rule predominantly comprise the isomer which is often undesirable, which then likewise necessitates an expensive separation process. Reaction of ethyl 2,4-dioxopentanecarboxylate with methylhydrazine thus gives a 1:1 mixture of 1,5-dimethyl-pyrazole-3-carboxylic acid ester and the corresponding 2,5-dimethylisomer (Austr. J. Chem. 36, 135–147 (1983)). Other authors report even more unfavorable ratios of 35:65 for this reaction (Chem. Ber. 59, 1282 (1926)), which have been confirmed in comparative laboratory studies. The same authors have achieved yet poorer results (isomer ratio 15:85) with analogous etherified enoles, for example with O-ethylacetone-oxalic ester and methylhydrazine. In these reactions, as a rule either the free hydrazines are employed with the diketo ester, or the sodium salt of the diketo ester (enolate) and hydrazine salts, from which the hydrazine is liberated with alkalis, such as sodium hydroxide or sodium carbonate, are employed.

The reaction mixtures obtained in preparation processes of the prior art cannot be worked up by distillation because they comprise by-products which render separation of the two isomers formed by distillation impossible.

There is therefore still the need for a process for selective preparation of 1-alkyl-pyrazole-5-carboxylic acid esters which are as far as possible isomer-free.

A process has now been found for the preparation of 1-alkyl-pyrazole-5-carboxylic acid esters of the formula (I)

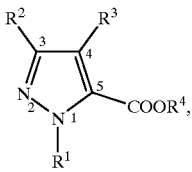

(I)

in which
$R^1$ and $R^4$ independently of one another each represent straight-chain or branched $C_1$–$C_6$-alkyl, $C_3$–$C_7$-cycloalkyl or optionally substituted $C_7$–$C_{12}$-aralkyl and
$R^2$ and $R^3$ independently of one another each represent hydrogen, straight-chain or branched $C_1$–$C_6$-alkyl, $C_3$–$C_7$-cycloalkyl or optionally substituted $C_7$–$C_{12}$-aralkyl,
which comprises reacting the enolate of a 2,4-diketocarboxylic acid ester of the formula

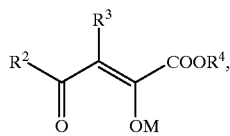

(II)

in which
$R^2$, $R^3$ and $R^4$ have the meaning given in the case of formula (I) and
M represents one equivalent of a metal atom,
with an N-alkylhydrazinium salt of the formula (III)

(III), $R^1$ has the meaning given in the case of formula (I) and
$R^5$ together with the $COO^\ominus$ moiety, represents the anion of an organic acid,
in the presence of a solvent.

$C_7$–$C_{12}$-aralkyl, and the benzyl preferred from this, and $C_6$–$C_{10}$-aryl (mentioned later), and the phenyl preferred from this (mentioned later) can in each case contain, for example, up to two substituents from the group consisting of halogen atoms and $C_1$–$C_4$-alkyl radicals.

Preferred diketocarboxylic acid ester enolates of the formula (II) are those in which the radicals $R^2$ and $R^3$ independently of one another in each case represent hydrogen, straight-chain or branched $C_1$–$C_4$-alkyl, $C_3$–$C_6$-cycloalkyl or optionally substituted benzyl, and those in which the radical $R^4$ represents straight-chain or branched $C_1$–$C_4$-alkyl.

Particularly preferred 2,4-diketocarboxylic acid ester enolates of the formula (II) are those in which $R^2$ and $R^4$ each represent $C_1$–$C_4$-alkyl and $R^3$ represents H.

M in the formula (II) preferably represents a monovalent metal atom or one equivalent of a divalent metal atom. Examples are lithium, sodium, potassium, calcium and magnesium. Sodium, lithium and magnesium are particularly preferred.

Preferred N-alkylhydrazinium salts of the formula (III) are those in which $R^1$ represents straight-chain or branched $C_1$–$C_4$-alkyl or optionally substituted benzyl and $R^5$ represents straight-chain or branched $C_1$–$C_6$-alkyl, $C_3$–$C_7$-cycloalkyl, $C_7$–$C_{12}$-aralkyl or $C_6$–$C_{10}$-aryl, which can optionally be substituted as mentioned above.

$R^5$, together with the $COO^\ominus$ moiety, can also represent an anion of a polybasic organic acid. Examples are anions of oxalic, malonic, succinic, glutaric, adipic, maleic, fumaric, malic, tartaric and citric acid, which can in each case be mono- or polyanions. Such anions can contain one or more $COO^\ominus$ moieties, and optionally additionally also COOH radicals. In the case of anions of polybasic organic acids, the alkylhydrazine can be employed in a ratio to the acid in equimolar amounts or in amounts which correspond to the number of acid groups.

The diketo ester enolates of the formula (II) can be prepared, for example, from the corresponding pure, isolated 2,4-diketo esters by addition of an alcoholate. Possible alcoholates are, for example, those which correspond to the formula (IV)

$$M(OR^6)_n \qquad (IV),$$

in which

M has the meaning given in the case of formula (II)

$R^6$ represents $C_1$–$C_4$-alkyl and n corresponds to the valency of M.

The preparation of the diketo ester enolates of the formula (II) can be carried out in a solvent, for example in water, and/or a $C_1$–$C_4$-alcohol.

Diketo ester enolates of the formula (II) can also be prepared by the customary method by condensation of a methyl alkyl ketone of the formula (V)

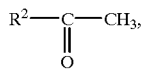

$$(V)$$

in which $R^2$ has the meaning given in the case of formula (I), with an oxalic ester of the formula $$R^4OOC—COOR^4 \qquad (VI)$$

in which $R^4$ has the meaning given in the case of formula (I).

Here also, the reaction is carried out in the presence of an alcoholate, for example an alcoholate of the formula (IV), and a solvent. The crude reaction mixture obtained by this reaction can be employed directly in the reaction with the N-alkylhydrazinium salt of the formula (III).

Possible solvents for the reaction of the methyl alkyl ketones of the formula (V) with oxalic esters of the formula (VI) and further reaction with the N-alkylhydrazinium salts of the formula (III) are, for example, alcohols, such as methanol, ethanol, isopropanol, n-propanol and n-, i-, s- and t-butanol. The alcoholate of the formula (IV) can be prepared by dissolving an alkali metal or alkaline earth metal M in the alcohol which corresponds to the alcoholate of the formula (IV).

The hydrazinium salt of the formula (III) can be prepared, for example, by mixing an alkylhydrazine of the formula (VII)

$$R^1—NH—NH_2 \qquad (VII),$$

in which $R^1$ has the meaning given in the case of formula (I), with a carboxylic acid of the formula (VIII)

$$R^5—COOH \qquad (VIII),$$

in which $R^5$ has the meaning given in the case of formula (III).

If appropriate, this reaction can be carried out with the addition of a solvent, for example an alcohol.

To prepare compounds of the formula (I), the enolate of the formula (II) and the N-alkylhydrazinium salt of the formula (III), both in the form of the solution obtained during their preparation, if appropriate, are brought together. Any portions of the enolates or of the N-alkylhydrazinium salts which tend to precipitate out can be dissolved again or kept in solution by heating and/or addition of further solvent. For example, an alcoholic enolate solution can be added to an N-alkylhydrazinium salt solution which has been initially introduced, or conversely, an N-alkylhydrazinium salt solution can be added to an enolate solution which has been initially introduced.

The total amounts of solvent employed are in general chosen such that stirrable suspensions or solutions are present. The amount of solvent per mole of reaction batch can be, for example, between 100 and 2000 ml. This amount is preferably 200 to 1000 ml, particularly preferably 250 to 500 ml.

The molar ratio for the reaction of the diketo ester enolates of the formula (II) with the N-alkylhydrazinium salts of the formula (III) can vary within wide limits, for example from 5:1 to 1:5. In a preferred embodiment, approximately equimolar amounts of diketo ester enolate of the formula (II) and N-alkylhydrazinium salt of the formula (III) are reacted, for example 0.9 to 1.1 mol of diketo ester enolate of the formula (II) per mole of N-alkylhydrazinium salt of the formula (III).

The amount of alcoholate for preparation of the diketo ester enolate can likewise vary within wide limits. It is preferably at least equimolar.

If the diketo ester is prepared in a previous step, as described above, from a ketone from the formula (V) and an oxalic acid ester of the formula (VI), the molar ratios thereof can also vary. A slight deficit, for example in each case a deficit of 1 to 10 mol %, of the ketone of the formula (V) based on the oxalic ester of the formula (VI) and the alcoholate of the formula (IV), is preferably used. The last two are preferably employed in approximately equimolar amounts with respect to one another. The molar ratios are then, for example, 0.9 to 0.99 mol of ketone of the formula (V) to 0.9 to 1.1 mol of oxalic acid ester of the formula (VI) to 1 mol of alcoholate of the formula (IV).

In the preparation of the N-alkylhydrazinium salt of the formula (III) from an alkylhydrazine of the formula (VII) and a carboxylic acid of the formula (VIII), the molar ratio of the two starting substances can likewise vary within wide limits. An amount of 1 to 1.5 mol of acid per mole of alkylhydrazine is preferred. It is particularly preferable to employ equimolar amounts of alkylhydrazine and carboxylic acid.

An excess of carboxylic acid of the formula (VIII) is advantageous if the alcoholate of the formula (IV) is present in excess. This alcoholate excess can then be neutralized with the excess acid.

The reaction temperatures for the reaction of the reaction partners of the formula (II) and (III) can be, for example, between −20 and +100° C., preferably between 0 and 80° C., particularly preferably between 20 and 50° C. This also applies to the temperatures during the subsequent stirring times.

The reaction times (bringing together of the reaction partners+subsequent stirring time) can be, for example, between 0.5 and 12 hours, preferably between 1 and 8 hours, particularly preferably between 2 and 5 hours. The following compounds of the formula (II) are preferably employed for the process according to the invention:

ethyl 2,4-diketopentanecarboxylate as the sodium, lithium, potassium or magnesium enolate, ethyl 2,4-diketohexanecarboxylate, ethyl 2,4-diketoheptanecarboxylate, ethyl 2,4-diketooctanecarboxylate and ethyl 2,4-diketo-3-ethylpentanecarboxylate (in each case in the form of their sodium, lithium, magnesium or potassium enolate salts), and methyl, n-propyl, i-propyl and n-, i-, s- and t-butyl esters of the abovementioned diketocarboxylic acids, likewise in the form of the enolate salts mentioned.

N-alkylhydrazinium salts of the formula (III) are preferably methylhydrazinium formate, acetate, propionate, butyrate, isobutyrate, benzoate, oxalate and succinate, N-propylhydrazinium formate, acetate, propionate, butyrate, isobutyrate and benzoate, ethylhydrazinium formate, acetate, propionate, butyrate, i-butyrate, benzoate, oxalate and succinate and the hydrazinium salts of i-propyl-, n-butyl-, t-butyl-, benzyl- and n-pentylhydrazine with the abovementioned carboxylic acid anions.

A general embodiment of the process according to the invention, explained by the reaction of ethyl 2,4-diketoheptanecarboxylate sodium salt with methylhydrazinium formate by way of example, is as follows:

order to prevent precipitation of the enolate, and is added to a previously prepared solution of methylhydrazinium formate in ethanol (initially introduce methylhydrazine into ethanol, add formic acid dropwise) in the course of 1 hour. The mixture is subsequently stirred for an appropriate time, the excess ethanol is distilled off, and water and toluene are added. The toluene phase is separated off, the aqueous phase is extracted twice more with toluene and, after the organic phases have been combined, these are reextracted with water. The toluene solution of the crude pyrazole is concentrated by distillation of the solvent, and the residue is subjected to fractional distillation in vacuo. The two isomeric pyrazoles can be isolated in the pure form without great expenditure on separation.

It is decidedly surprising that the use of the N-alkylhydrazinium salts instead of free hydrazines for the preparation of N-alkylpyrazoles reverses the regioselectivity. As illustrated in the following equation, according to the prior art, if free alkyl hydrazines are employed (it is irrelevant whether they are employed as such or liberated from their salts by alkali metal hydroxide solutions), the undesirable isomer with the alkyl radical on the nitrogen further from the carboxyl group is preferentially formed, while the process according to the invention preferentially gives the desired isomer (I) in which the alkyl group is on the nitrogen closest to the carbonyl group in the pyrazole.

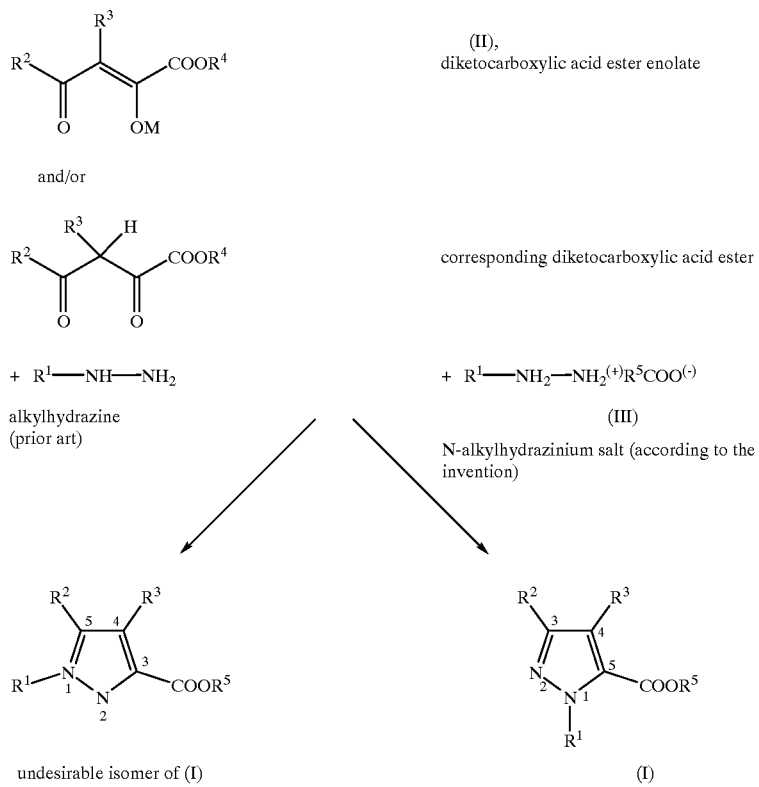

The sodium salt of ethyl 2,4-diketoheptanecarboxylate is prepared from 2-pentanone and oxalic ester with sodium methylate as an auxiliary base in ethanol analogously to known instructions (see, for example, Organicum, 19th edition, page 490 (1993)). This solution is kept at 50° C. in The process according to the invention allows more controlled preparation of substituted 1-alkyl-pyrazole-5-carboxylic acid esters. Compared with the customary method—cyclization of 2,4-diketo esters with hydrazine and subsequent N-alkylation—this process saves the alkylation step, which necessitates expensive intermediate isolation of the hydrazine reaction product and expensive working up of the alkylation batch. The process according to the invention is particularly advantageous due to the possibility of a simple separation by distillation for isolation of the desired product from the reaction mixture, avoids waste products and, due to its shortness, is energy-saving. This makes the known direct reaction of the diketo esters with alkylhydrazines particularly economic due to a drastic shift in the isomer ratios in favor of the desired product. 1-alkyl-pyrazole-5-carboxylic acid esters of the formula (I) are valuable intermediate products for the preparation of pharmaceutical active compounds having a vaso-modifying and/or spasmolytic action (see EP-OS (European published specification) 463 756, EP-OS (European published specification) 526 004 and DE-OS (German published specification) 19 27 429) and for the preparation of pesticides having an insecticidal and acaricidal action (see JP-OS (Japanese published specification) 89–114 466).

EXAMPLES

Example 1

Ethyl 1-methyl-3-n-propyl-pyrazole-5-carboxylate 340 g of 20% strength by weight sodium ethylate solution in ethanol were initially introduced into a 1 1 4-necked flask and a mixture of 78 g of 2-pentanone and 146.1 g of diethyl oxalate was added dropwise in the course of 1 hour, while stirring. When the addition was complete, 100 ml of ethanol were added and the mixture was subsequently stirred under reflex for a further hour and then cooled to 50° C. During the subsequent stirring time, 41.5 g of methylhydrazine and 50 ml of ethanol were initially introduced into a 1 1 4-necked flask and 41.4 g of formic acid were added dropwise in the course of 15 minutes, with external cooling. The crude ethyl 2,4-diketoheptanecarboxylate enolate solution prepared as described above was now added to this mixture, the solution being kept at 30 to 40° during the addition in order to prevent the enolate salt from crystallizing out. The temperature of the initial mixture was kept between 30 and 35° C. during the addition. The addition had ended after 1 hour. The suspension present became thinner and thinner in the course of the addition of the ester enolate solution. After the mixture had been subsequently stirred at 30° C. for a further hour, 4.5 g of formic acid were added, the mixture was heated and ethanol was distilled off up to a bottom temperature of 110° C. 505 g of ethanol were obtained. The readily stirrable suspension was cooled to room temperature, and 400 ml of water and 200 ml of toluene were added. The organic phase was separated off and the aqueous phase was extracted with 200 ml of toluene. The combined organic phases were washed with 100 ml of water and the toluene was distilled off. The residue (173.1 g—isomer ratio of 4.5:1 of ethyl 1-methyl-3-n-propyl-pyrazole-5-carboxylate to ethyl 1-methyl-5-n-propyl-pyrazole-3-carboxylate), a deep brown oil, was separated into the individual components by fractional distillation. 98 g of the desired product were obtained in a purity of 98.9% by weight (determined by gas chromatography). This corresponds to a yield of 56.2% of theory.

Example 2 (For Comparison)

37.3 g of ethyl 2,4-diketoheptanecarboxylate were initially introduced into 75 ml of ethanol, and a solution of 9.2 g of methylhydrazine in 25 ml of ethanol was added in the course of 15 minutes, with external cooling at 20° C. When the addition was complete, the mixture was heated under reflux for 1 hour and then cooled again to room temperature. Analysis of the reaction mixture by gas chromatography showed a ratio of ethyl 1-methyl-5-n-propyl-pyrazole-3-carboxylate (undesirable product) to ethyl 1-methyl-3-n-propyl-pyrazole-5-carboxylate (desired product) of 4:1. After this finding, the reaction mixture was no longer worked up.

Example 3

Ethyl 1-methyl-3-n-propyl-pyrazole-5-carboxylate 76.5 g of 20% strength by weight sodium ethylate solution were initially introduced into a 250 ml 4-necked flask and 41.9 g of ethyl 2,4-diketoheptanecarboxylate were added in the course of 15 minutes. The solution thus prepared was added to a mixture of methylhydrazine (10.4 g), acetic acid (13.5 g) and ethanol (20 ml) at an internal temperature of 30 to 40° C. in the course of 45 minutes. When the addition was complete, the mixture was subsequently stirred at room temperature for a further hour and the ethanol was then distilled off. 100 ml of toluene and 100 ml of water were then added, the phases which form were separated and the aqueous phase was extracted twice more with 50 ml of toluene each time. The combined toluene extracts were reextracted with 100 ml of water, dried and concentrated under a slight vacuum. 31 g of isomer-free ethyl 1-methyl-3-n-propyl-pyrazole-5-carboxylate having a boiling point of 125 to 128° C. under a pressure of 13 mm were obtained by fractional distillation. This corresponds to a yield of 75% of theory. The undesirable isomer ethyl 1-methyl-5-n-propyl-pyrazole-3-carboxylate was obtained as a second fraction in a yield of 6.2 g (=15% of theory). The boiling point of this isomer was 166 to 168° C. under a pressure of 13 mm.

What is claimed is:

1. A process for the preparation of a 1-alkyl-pyrazole-5-carboxylic acid ester of the formula (I)

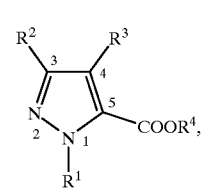

(I)

in which
$R^1$ and $R^4$ independently of one another each represent straight-chain or branched $C_1$–$C_6$-alkyl, $C_3$–$C_7$-cycloalkyl or optionally substituted $C_7$–$C_{12}$-aralkyl and
$R^2$ and $R^3$ independently of one another each represent hydrogen, straight-chain or branched $C_1$–$C_6$-alkyl, $C_3$–$C_7$-cycloalkyl or optionally substituted $C_7$–$C_{12}$-aralkyl, which comprises reacting the enolate of a 2,4-diketocarboxylic acid ester of the formula

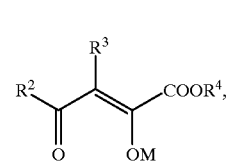

(II)

in which
$R^2$, $R^3$ and $R^4$ have the meaning given in the case of formula (I) and M represents one equivalent of a metal atom,
with an N-alkylhydrazinium salt of the formula (III)

$$R^1-NH_2-NH_2^{\oplus} \ R^5COO^{\ominus} \qquad (III),$$

in which
$R^1$ has the meaning given in the case of formula (I) and
$R^5$ together with the $COO^{\ominus}$ moiety, represents the anion of an organic acid,
in the presence of a solvent.

2. The process as claimed in claim 1, wherein the diketocarboxylic acid ester enolate of the formula (II) is one in which the radicals $R^2$ and $R^3$ independently of one another in each case represent hydrogen, straight-chain or branched $C_1$–$C_4$-alkyl, $C_3$–$C_6$-cycloalkyl, benzyl or substituted benzyl, or one in which the radical $R^4$ represents straight-chain or branched $C_1$–$C_4$-alkyl.

3. The process as claimed in claim 1, in which M in the formula (II) represents lithium, sodium, potassium, calcium or magnesium.

4. The process as claimed in claim 1, wherein the N-alkylhydrazinium salt of the formula (III) is one in which $R^1$ represents straight-chain or branched $C_1$–$C_4$-alkyl, benzyl or substituted benzyl and $R^5$ represents straight-chain or branched $C_1$–$C_6$-alkyl, $C_3$–$C_7$-cycloalkyl, $C_7$–$C_{12}$-aralkyl or $C_6$–$C_{10}$-aryl, which is unsubstituted or substituted and which, together with the $COO^{\ominus}$ moiety, represents the anion of an organic acid.

5. The process as claimed in claim 1, wherein, in formula (III), $R^5$, together with the $COO^{\ominus}$ moiety, represents an anion of a polybasic organic acid.

6. The process as claimed in claim 1, wherein in formula (III), $R^5$, together with the $COO^{\ominus}$ moiety, represents an anion of oxalic, malonic, succinic, glutaric, adipic, maleic, fumaric, malic, tartaric or citric acid.

7. The process as claimed in claim 1, wherein the diketo ester enolate of the formula (II) is prepared from the corresponding pure, isolated 2,4-diketo ester by addition of an alcoholate in the presence of a solvent.

8. The process as claimed in claim 1, wherein portions of the enolate which tend to precipitate are dissolved again or kept in solution by either heating or addition of further solvent or both.

9. The process as claimed in claim 1, wherein portions of the N-alkylhydrazinium salt which tend to precipitate are dissolved again or kept in solution by either heating or addition of further solvent or both.

10. The process as claimed in claim 1, wherein a 100 to 2000 ml of solvent are present per mole of reaction batch.

11. The process as claimed in claim 1, wherein the molar ratio for the reaction of the diketo ester enolate of the formula (II) with the N-alkylhydrazinium salt of the formula (III) is between 5:1 and 1:5 and wherein the diketo enolate of formula (II) is prepared by the addition reaction of an alcoholate of the formula (IV)

$$M(OR^6)_n \qquad (IV),$$

in which
M has the meaning given in the case of formula (II)
$R^6$ represents $C_1$–$C_4$-alkyl and
n corresponds to the valency of M
with the corresponding 2-4-diketo esters: the amount of alcoholate present during the reaction being at least equimolar, or by condensation of a methylalkylketone of the formula (V)

$$R^2-\underset{\underset{O}{\|}}{C}-CH_3, \qquad (V)$$

in which
$R^2$ has the meaning given in the case of formula (I),
with an oxalic ester of the formula $$R^4OOC-COOR^4 \qquad (VI)$$

in which
$R^4$ has the meaning given in the case of formula (I) in the presence of the alcoholate of the formula (IV)
the molar ratio being 0.9 to 0.99 mol of ketone of the formula (V) to 0.9 to 1.1 mol of oxalic acid ester of the formula (VI) to 1 mol of alcoholate of the formula (IV).

12. The process as claimed in claim 1, wherein the reaction temperature for the reaction of the reaction partners of the formulae (II) and (III) is between –20 and +100° C. and the reaction time is between 0.5 and 12 hours.

13. The process of claim 1, wherein $R^1$ is $C_1$–$C_6$-alkyl or $C_3$–$C_7$-cycloalkyl.

14. The process of claim 1, wherein $R^5$ is straight-chain or branched $C_1$–$C_6$-alkyl.

* * * * *